United States Patent [19]

Hughes

[11] Patent Number: 5,129,823
[45] Date of Patent: Jul. 14, 1992

[54] DRIVER TOOL AND METHOD FOR IMPLANT DENTISTRY

[75] Inventor: John G. Hughes, Winter Park, Fla.

[73] Assignee: R & J Innovations, Inc., Maitland, Fla.

[21] Appl. No.: 773,156

[22] Filed: Oct. 8, 1991

[51] Int. Cl.⁵ .................. A61C 3/00; A61C 8/00
[52] U.S. Cl. .................. 433/141; 433/147; 433/173
[58] Field of Search .......... 433/173, 174, 141, 147; 81/57.3

[56] References Cited

U.S. PATENT DOCUMENTS

| | | | |
|---|---|---|---|
| 2,830,479 | 4/1958 | Finn | 81/57.3 |
| 3,283,621 | 11/1966 | Faso | 81/57.3 |
| 3,852,884 | 12/1974 | Lazarus | 433/141 |
| 4,735,119 | 4/1988 | Riley | 81/57.3 |
| 4,976,617 | 12/1990 | Carchidi | 433/141 |
| 4,995,810 | 2/1991 | Soderberg | 433/141 |
| 5,030,096 | 8/1991 | Hurson et al. | 433/173 |

FOREIGN PATENT DOCUMENTS 0230326 8/1987 European Pat. Off. ............ 433/147

*Primary Examiner*—Gene Mancene
*Assistant Examiner*—Cindy A. Cherichetti
*Attorney, Agent, or Firm*—Warren L. Franz

[57] ABSTRACT

A tool for the installation of an abutment or screw in implant dentistry has a knob manually rotatable externally of a patient's mouth on one end of an arm and a bit, releasably secured on a sprocket, rotatable inside the patient's mouth in response to rotation of the knob. A chain connects the bit sprocket to a sprocket attached to the knob, so that the bit rotates about an axis parallel to, but laterally offset by the arm from, the axis of rotation of the knob. A resilient elastomer sleeve is releasably stretched over the abutment or screw and over the bit for initial positioning. Mutliple, interchangeable bits are provided to match different sized abutment or screw heads. The bit shank is recessed intermediate cylindrical portions, for receiving a set screw.

16 Claims, 1 Drawing Sheet

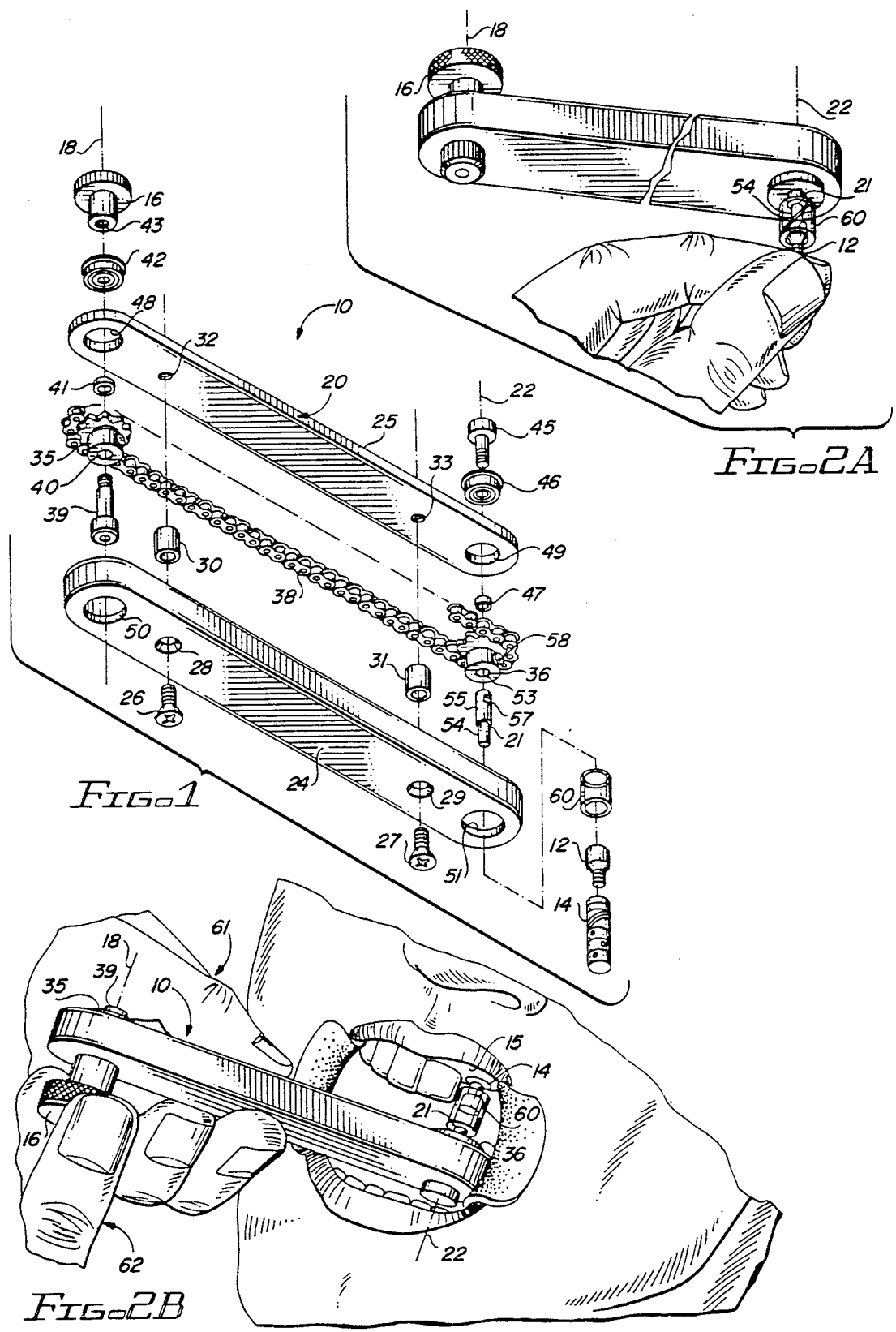

DRIVER TOOL AND METHOD FOR IMPLANT DENTISTRY

This invention relates generally to a driver tool and method for installation of abutments and screws in implant dentistry; and, more particularly, to a hand-operated tool having interchangeable bits that can be manipulated within the mouth of the patient by hand movements executed externally.

BACKGROUND OF THE INVENTION

The installation of abutments and screws within the mouth in implant dentistry is both stressful and hazardous. The mouth has a small opening relative to a dentist's hands, and is a difficult place to work. Implant abutments and screws are difficult to grasp, and great care must be taken that the same are not swallowed or aspirated by the patient.

The screwing of abutments (or posts) onto the implant structure or threading of screws into the bone is conventionally undertaken by small flat or allen head screwdrivers which have shanks and handles sized to fit within the mouth, and which are gripped and rotated within the mouth by the dentist's hand. Such tools have the advantage that the tightening action can be "felt" by the dentist, and carefully controlled. They are, however, difficult to manipulate in such close quarters and, if dropped, can become lodged in the patient's throat. Their use, thus, requires much concentration and is exhausting.

The use of ratchet-type wrenches for installation of abutments and screws is known, though the same offer relatively little advantage over the straight shank direct application screwdrivers. The ratchet action offers less control because is interferes with the "feel" or tactile sensitivity of the installation, and the ratcheting movement introduces undesirable instability in a sensitive procedure. (In ratcheting, the dentist is unable to get the desired tactile feedback regarding torque resistance of the meshing threads, etc.) The use of screwdriver bits on electrical dental handpieces is likewise undesirable because of the complete loss of tactile sensitivity with the attendant risk of either breaking the screw or spinning the implant in the bone.

SUMMARY OF THE INVENTION

It is an object of the invention to provide a hand-operated driving tool and method for the installation of threaded abutments and screws in implant dentistry, that provides an offset so that bits can be manipulated within the mouth by direct positive drive of hand movements executed outside the mouth.

In accordance with the invention, a dental handtool for the installation of implant abutments and screws comprises an offset screwdriver including a hand-grippable drive member mounted for manual rotation about a first axis at one end of an elongated structural element, a driver head or the like bit member mounted for rotation about a second axis parallel to the first axis, at the other end of the structural element, and torque transmission means connecting the drive member and the bit, so that hand rotation of the rotary member about the first axis will cause like rotation of the bit about the second axis, laterally offset by the structural member from the first axis.

In a preferred embodiment of the invention, described in greater detail below, the tool resembles a hand-held screwdriver, where the hand-grippable rotary member serves the function of the screwdriver handle and the bit member serves the function of the screwdriver shank and head, with the shank and head rotating directly in correspondence with rotation of the handle, but in offset relationship thereto. The hand-grippable member is mounted for rotation relative to the elongated structural element by attachment to a first sprocket. The driver head is provided by a plurality of interchangeable bits which can be releasably secured within the bore of a second sprocket member. Torque transmission between the first and second sprockets is provided by a fully autoclavible, stainless steel, unlubricated roller chain. The bit shanks are provided with reduced intermediate portions, against which a set screw extending radially of the second sprocket bore can be tightened. Enlargements of the shaft above and below the flat region prevent loss of the bit during use, even if the set screw becomes slightly loosened. A resilient elastomer retainer sleeve is fitted about the shank and about the abutment or screw to hold the latter in place on the bit head during the installation procedure. Stability is advantageously benefitted by the use of X-bearings which support moment, thrust (axial) and radial loads during operation.

The invention provides an apparatus and a method for the installation of dental implant abutments and screws with the same "feel" and control as conventional hand-held dental screwdrivers, with greater capability for maneuverability, and with reduced risk of tool or screw swallowing or aspiration, thereby greatly reducing the anxiety and stress associated with such installation.

BRIEF DESCRIPTION OF THE DRAWINGS

Embodiments of the apparatus and method of the invention have been chosen for purposes of illustration and description, and are shown in the accompanying drawings, wherein:

FIG. 1 is an exploded view of a driver tool in accordance with the invention; and FIGS. 2A-2B are views showing the steps in a method of installing an implant abutment or screw according to the invention, utilizing the tool of FIG. 1.

Throughout the drawings, like elements are referred to by like numerals.

DETAILED DESCRIPTION OF PREFERRED EMBODIMENTS

The principles of the apparatus and method of the invention are illustrated, by way of example, with reference to an embodiment of a driver tool 10 (FIG. 1) which can be utilized in accordance with the steps of an embodiment of a method for the installation of an abutment or screw 12 into a dental implant 14 fixed at an implantation site of a patient's mandible or maxilla bone 15 (FIG. 2B).

The tool 10, as shown in FIG. 1, comprises a hand-grippable cylindrical member, in the form or a knurled knob 16, mounted for manual rotation about an axis 18 at one end of an elongated structural element or arm 20. An implant abutment or screw driver bit 21 is releasably mounted for rotation about an axis 22 adjacent the other end of the support structure 20. Means is provided for driving the rotation of the bit 21 directly and positively in response to manual rotation of the knob 16. The tool 10, thus, functions in the manner of a conventional dental screwdriver, with the knob 16 serving the role of the screwdriver handle and the bit 21 serving the role of the screwdriver shank and head. Unlike the conventional screwdriver, however, the structure 20 serves to laterally offset the axis 18 of rotation of the handle 16 from the axis 22 of rotation of the shank/head bit 21. Moreover, whereas with conventional screwdrivers wherein a different screwdriver must be used to match the size and type (allen head or slotted) of the head of the threaded fastener 12, with tool 10 different head sizes and types are accommodated merely by selecting a different one of a plurality of interchangeable bits 21.

For the shown embodiment of tool 10, the structural element 20 comprises a lineally extending, thin profile arm having a hollow housing cover portion 24 that matches a planar structural bar 25 (FIG. 1). The bar 25 is fastened over the interior opening of the housing 24 by conventional means, such as screws 26, 27 that thread through housing bores 28, 29 and spacer sleeves 30, 31 into corresponding bores 32, 33. The bores 28, 29 are countersunk and the external surfaces of the housing 24 and bar 25 are rounded to avoid sharp or jagged edges or points that might injure the dentist or patient during the abutment/screw installation procedure. All components are stainless steel of surgical quality suitable for heat disinfection and the use of oils or other lubricants is minimized or, if possible, avoided altogether.

The means illustrated in FIG. 1 for directly and positively transmitting torque between the knob 16 and the bit 21 comprises a drive sprocket 35, a driven sprocket 36 and an unlubricated length of roller chain 38 extending circumferentially about the respective runs of teeth of both sprockets 35, 36. Sprockets 35, 36 are mounted relative to the planar bar 25, so that the rotational axes 18, 22 are generally perpendicular to the plane of the cover and the run of chain is generally parallel thereto. As shown in FIG. 1, sprocket 35 is attached to bar 25 by means of an allenhead screw 39 which projects upwardly through an axial bore 40 of sprocket 35, through the bores of a spacer 41 and an inner race of an X-bearing 42, and into a threaded blind axial bore 43 of a stem of knob 16. Sprocket 36 is attached to the bar 25 by means of an allenhead screw 45 that threads through the axial bores of an inner race of an X-bearing 46 and spacer 47, and into the top of a bore of sprocket 36. The X-bearings 42, 46 are press fitted into bores 48, 49 formed adjacent the respective ends of the bar 25. Slightly larger bores 50, 51 are provided for clearance purposes on corresponding locations adjacent the ends of housing 24. Bores 48, 50 and 49, 51 are formed respectively coaxially with the axes 18, 22. The tool 10 is configured so that the knob 16 projects outwardly adjacent one end on one side of structure 20 (upwardly at left end and top side as seen in FIG. 1) and a bit receiving bore 53 of sprocket 36 is accessible adjacent the opposite end on an opposite side of structure 20 (from below at right end and on the bottom side as seen in FIG. 1).

The bits 21 have a head end 54 and a shank end 55. For a plurality of interchangeable bits, each head end 54 is differently configured. For example, a set of bits 21 may include several different sized allenheads and several different sized flat heads. A selection of six bits can be made, so that a bit is available to match most commercially available abutments/screws. The bit shanks 55 are uniformly sized from bit to bit to fit within the bore 53 of sprocket 36. Each shank is configured with a recessed flat portion 57 (segment-shaped in cross-section), intermediate circular cross-sectioned upper and lower remaining portions of the otherwise generally cylindrical shank 55. The shank of a selected bit 21 is releasably retained within the sprocket bore 53 by means of an allenhead set screw 58 that threads radially against the flat 57. Having larger cross-sectioned portions of shank 55 above and below the flats 57, reduces the risk that a bit 21 will fall out of the tool 10 during an installation procedure, even though the set screw 58 should become slightly loosened.

To hold an abutment or screw 12 onto the head 54 of a bit 21 during installation, the invention advantageously provides resilient transparent elastomer sleeves or retainers 60 that have inner bores that may be simultaneously elastically drawn over a bottom portion of shank 55 of bit 21 and a top portion of the head of an abutment or screw 12. The sleeves 60 are provided in various sizes to match the sizes of the bits 21 and fasteners 12.

In operation, as shown in FIG. 2A, the top of the head of an abutment or screw 12 is fitted onto the head 54 of a matching bit 21 of the tool 10 and held in place by the bottom portion of the stretched inside bore of retainer 60, whose stretched top portion is drawn up onto the shank 55 of the selected bit 21. The threaded end of the abutment or screw 12 is then inserted into the exposed bore of the implant 14 which is already located in the bone 15 of a patient's mouth, as shown in FIG. 2B.

The location of the die end of the structure 10 within the patient's mouth is supported by the fingers of one hand 61 of the user, while the knurled circumferential portion of the knob 16 at the other end of the structure 10 outside the patient's mouth is grasped between the thumb and forefinger of the user's other hand 62. Clockwise rotation of the knurled knob 16 by the thumb and forefinger of the hand 62 will cause corresponding like clockwise rotation of the bit 21, for tightening of the threaded abutment or screw 12. The feeling to the user upon turning the knob 16 will be the same as if the handle of a conventional dental screwdriver directly connected to the abutment or screw 12 were being turned. Rotation of knob 16, rotates sprocket 35 which is connected by means of chain 38 to drive sprocket 36 in like rotational direction. Die 21, which is fixed by means of set screw 58 in contact with recess 57, rotates with rotation of sprocket 36. Unlike conventional ratcheting mechanisms, the elongated arm of structure 20 can be maintained motionless during the installation procedure. As the abutment or screw 12 becomes embedded, the screw retaining sleeve is pushed back onto the shank 55 of the bit 21, so that it loses its grip on the abutment or screw 12, releasing the same. The elasticity of the sleeve 60 is chosen so that it will hold the fastener 12 onto the bit through commencement of installation, but will release the same as installation is completed.

There are, or course, other torque transmission means that can be used to accomplish the same torque transmission function to provide the offset between rotation of the knurled knob 16 and corresponding rotation of the releasably held bit 21. For instance, the knob 16 and die 21 could each be coupled to bevel gears, which are then respectively coupled to further bevel gears located at the ends of a rotating shaft that extends between the ends of the arm 20.

Those skilled in the art to which the invention relates will appreciate that other substitutions and modifications can also be made to the described embodiment without departing from the spirit and scope of the invention as described by the claims below.

What is claimed is:

1. A tool for the installation of an abutment, screw or similar fastener during implant dentistry or the like, comprising:
    an elongated structural element having opposite ends and opposite sides;
    a member rotatably mounted adjacent one end of said element and being hand-grippable from ne side of said element for rotation about a first axis transverse to the elongation of said element;
    a bit having a shank portion and a head portion, said head portion being dimensioned, configured and adapted to mate with the fastener for rotation of the fastener when said head portion is rotated;
    a resilient elastomer sleeve having an internal bore dimensioned, configured and adapted to be simultaneously stretched over said bit and over the fastener, to releasably hold the fastener in mating engagement with said head portion of said bit;
    means, accessible from the other side of said element, for releasably rotatably securing said bit adjacent the other end of said element for rotation about a second axis parallel to and laterally-spaced in the direction of said elongation from said first axis; and
    torque transmission means directly and positively connecting said hand-grippable member and said releasably securing means so that manual rotation of said hand-grippable member causes like rotation of said bit secured within said releasably securing means.

2. A tool as in claim 1, wherein said shank portion includes two cylindrical portions and a recessed portion intermediate said two cylindrical portions, and said means for releasably securing said bit comprises a rotating member having a bore within which said cylindrical portions are fitted, and a set screw selectively projectable into said bore and against, said recessed portion.

3. A tool as in claim 1, wherein said torque transmission means comprises a first sprocket attached to said rotatably mounted member; a second sprocket attached to said releasably securing means; and a chain connecting said first and second sprockets so that rotation of said first sprocket will cause corresponding rotation of said second sprocket.

4. A tool as in claim 3, wherein said means for releasably securing said bit comprises said second sprocket having a central bore coaxial with said second axis, and means for releasably retaining said shank portion within said central bore.

5. A tool as in claim 4, wherein said rotatably mounted member comprises a knurled knob coaxially mounted for rotation with said first sprocket.

6. A tool as in claim 4, wherein said shank portion includes two cylindrical portions and a recessed portion intermediate said two cylindrical portions, and said means for releasably retaining said shank portion within said central bore comprises a set screw selectively projectable into said central bore and against said recessed portion.

7. A tool as in claim 6, wherein said structural element comprises a generally planar member, and said first and second axes are perpendicular to the plane of said planar member.

8. A tool as in claim 7, wherein said knurled knob is mounted on said one side of said planar member and said central bore faces said other side of said planar member for receiving said shank portion.

9. A method for the installation of an abutment, screw or similar fastener during implant dentistry or the like, said method comprising the steps of:
    providing a dental tool having an elongated arm with opposite ends and opposite sides; a hand-grippable member rotatably mounted adjacent one end on said arm; a bit rotatably mounted adjacent said other end on said arm, said bit including a head portion dimensioned, configured and adapted to mate with the fastener; and torque transmission means connecting said hand-grippable member and said bit, so that rotation of said hand-grippable member causes like rotation of said bit;
    positioning the fastener at an implant site within the mouth of a patient;
    placing said arm with said one end located outside of the patient's mouth and with said other end located within the patient's mouth, said head portion in mating engagement with the fastener positioned at the implant site;
    holding said arm at a position intermediate said arm ends;
    manually rotating said hand-grippable member to rotate said bit; thereby rotating the fastener into its installed position.

10. A method as in claim 9, wherein said providing step further comprises providing a resilient elastomer sleeve having an internal bore, and said fastener positioning step comprises stretching said internal bore over said bit and over the fastener to hold said head portion in mating engagement with the fastener.

11. A method as in claim 9, wherein in said providing step, said bit comprises a removable element; said tool further comprises means for releasably rotatably securing said bit adjacent said other end; and wherein said method further comprises manipulating said releasably securing means to releasably secure said bit to said tool.

12. A method as in claim 11, wherein in said providing step said bit has a shank portion, including two cylindrical portions and a recessed portion intermediate said two cylindrical portions; said means for releasably securing said bit comprises a rotating member having a central bore; and said manipulating step comprises fitting said cylindrical portions within said central bore and tightening a set screw against said recessed portion.

13. A method as in claim 12, wherein said providing step further comprises providing a resilient elastomer sleeve having an internal bore, and said fastener positioning step comprises stretching said internal bore over said bit and over the fastener to hold said head portion in mating engagement with the fastener.

14. A method as in claim 9, wherein said dental tool provided in said providing step has said hand-grippable member mounted on one of said opposite sides, and said bit rotatably mounted on the other of said opposite sides; in said holding step, said arm is grasped with one hand; and in said manually rotating step said hand-grippable member is manually rotated with the other hand.

15. A method for the installation of an abutment, screw or similar fastener during implant dentistry or the like, said method comprising:
    providing a dental tool having an elongated arm with opposite ends and opposite generally planar parallel sides; a knurled knob; a first sprocket attached to said knurled knob; means mounting said knob on one of said sides adjacent one of said ends for rotation about a first axis perpendicular to said parallel sides; a bit, including a head portion dimensioned, configured and adapted to mate with the fastener; a second sprocket attached to said bit; means mounting said second sprocket one the other of said ends for rotation of said bit about a second axis parallel to and laterally-spaced in the direction of elongation of said arm from said first axis; and a roller chain connecting said first and second sprockets, so that rotation of said knob will cause rotation of said bit;

providing a resilient elastomer sleeve having an internal bore;

stretching said internal bore over said bit and over the fastener to hold said head portion in mating engagement with the fastener;

positioning the fastener held by said sleeve at an implant site within the mouth of a patient, with said arm positioned so that said one end is located outside of the patient's mouth and said other end is located within the patient's mouth;

holding said arm grasped with one hand at a position intermediate said arm ends;

manually rotating said knob with the other hand, to rotate said bit; thereby rotating the fastener into its installed position;

releasing said sleeve from the fastener; and withdrawing the tool and sleeve attached to the bit out of the patient's mouth.

16. A tool for the installation of an abutment, screw or similar fastener during implant dentistry or the like, comprising:

an elongated structural element having opposite ends and opposite sides;

a member rotatably mounted adjacent one end of said element and being hand-grippable from one side of said element for rotation about a first axis transverse to the elongation of said element;

a bit having a shank portion and a head portion, said head portion being dimensioned, configured and adapted to mate with the fastener for rotation of the fastener when said head portion is rotated;

means, accessible from the other side of said element, for releasable rotatably securing said bit adjacent the other end of said element for rotation about a second axis parallel to and laterally-spaced in the direction of said elongation from said first axis; and torque transmission means directly and positively connecting said hand-grippable member and said releasably securing means so that manual rotation of said hand-grippable member causes like rotation of said bit secured within said releasably securing means;

said torque transmission means including first and second X-bearings, each having inner and outer races; said outer race of said first X-bearing being attached to said element adjacent said one end and said outer race of said second X-bearing being attached to said structural element of said other end; a first sprocket attached to said inner race of said first X-bearing and to said rotatably mounted member; a second sprocket attached to said inner race of said second X-bearing and to said releasably securing means; and a chain connecting said first and second sprockets so that rotation of said first sprocket will cause corresponding rotation of said second sprocket.

* * * * *

UNITED STATES PATENT AND TRADEMARK OFFICE
CERTIFICATE OF CORRECTION

PATENT NO. : 5,129,823
DATED : JULY 14, 1992
INVENTOR(S) : HUGHES, JOHN G.

It is certified that error appears in the above-identified patent and that said Letters Patent is hereby corrected as shown below:

Cover Page, Item [75] Inventor, add --James R. Myers, Altamonte Springs, Fla.-- as coinventor.

Column 5:

Claim 1, line 10, change "ne" to --one--.

Claim 2, line 40, after "against" delete ",".

Signed and Sealed this

Eleventh Day of July, 1995

Attest:

BRUCE LEHMAN

Attesting Officer     Commissioner of Patents and Trademarks